(12) United States Patent  
Elbert et al.

(10) Patent No.: US 6,743,207 B2  
(45) Date of Patent: Jun. 1, 2004

(54) APPARATUS AND METHOD FOR THE INSERTION OF A MEDICAL DEVICE

(75) Inventors: Linda D. Elbert, Bloomington, IN (US); D. H. Perkins, Bountiful, UT (US); Srinivas Nishtala, Westford, MA (US); Stéphane Gobron, Mount Prospect, IL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 282 days.

(21) Appl. No.: 09/837,481

(22) Filed: Apr. 19, 2001

(65) Prior Publication Data

US 2002/0165553 A1 Nov. 7, 2002

(51) Int. Cl.$^7$ .............................................. A61M 5/178
(52) U.S. Cl. ............................ 604/164.04; 604/164.01; 604/164.09; 604/164.1; 604/164.11; 604/174; 606/185
(58) Field of Search ................................ 604/104–107, 604/109, 164.01, 164.03, 164.06, 164.08, 164.09, 164.1, 164.11, 164.12, 165.01, 165.02, 174, 164.04, 264; 606/167, 184, 185, 190, 191, 198

(56) References Cited

U.S. PATENT DOCUMENTS

| | | | | |
|---|---|---|---|---|
| 5,147,316 A | * | 9/1992 | Castillenti | .................... 604/164 |
| 5,330,497 A | * | 7/1994 | Freitas et al. | ................ 606/185 |
| 5,356,382 A | | 10/1994 | Picha et al. | |
| 5,429,598 A | | 7/1995 | Waxman et al. | |
| 5,830,125 A | * | 11/1998 | Scribner et al. | ............. 606/139 |
| 5,882,340 A | * | 3/1999 | Yoon | ..................... 604/164.12 |
| 5,935,107 A | | 8/1999 | Taylor et al. | |

FOREIGN PATENT DOCUMENTS

WO     WO 92 08513     5/1992

OTHER PUBLICATIONS

PCT International Search Report, International Application No. PCT/US02/01935, Jan. 25, 2002.

* cited by examiner

Primary Examiner—Brian L. Casler  
Assistant Examiner—Jennifer Maynard  
(74) Attorney, Agent, or Firm—Kenyon & Kenyon

(57) ABSTRACT

An apparatus and method for use in the percutaneous insertion of medical devices is disclosed. In an embodiment, the apparatus includes an access tube defining a central lumen and a retention portion disposed at a distal end of the access tube. The retention portion is reconfigurable between a first configuration of reduced lateral extent and a second configuration of increased lateral extent. A trocar is moveably disposed within the central lumen of the access tube. The access tube is movably disposed within a central lumen of an overtube. In an embodiment of a method of the present invention, the method includes the steps of inserting the trocar and access tube through a body wall of a patient, where the trocar is disposed within the access tube and where a retention portion disposed at a distal end of the access tube is configured in a first configuration of reduced lateral extent. The retention portion is then configured in a second configuration of increased lateral extent. The trocar is removed from the access tube. An overtube is inserted around the access tube and through the body wall, where the access tube is received within a central lumen of the overtube and where the retention portion is received through a slot defined by the overtube. The retention portion is returned to the first configuration of reduced lateral extent. The access tube is removed from the central lumen of the overtube and the medical device is inserted within the central lumen of the overtube and through the body wall. The overtube is then removed.

16 Claims, 5 Drawing Sheets

APPARATUS AND METHOD FOR THE INSERTION OF A MEDICAL DEVICE

BACKGROUND OF THE INVENTION

1. Field of the Invention

The present invention relates generally to an apparatus and method for use in the percutaneous insertion of medical devices. More specifically, the present invention relates to a gastro-intestinal tube placement device which includes a trocar, an access tube having an internal retention portion at its distal end for engaging an internal gastric wall, and an overtube.

2. Description of the Related Art

Medical practitioners utilize a variety of gastro-intestinal devices to access the gastro-intestinal tract. One type of gastro-intestinal device, the gastro-intestinal tube or gastrostomy tube, is widely used with patients who require catheterization for the purposes of, for example, delivering food or medication to the gastro-intestinal tract, draining the tract, or creating a surgical port.

Medical practitioners often use Percutaneous Endoscopic Gastrostomy (PEG) techniques, such as those described in U.S. Pat. Nos. 4,861,334; 4,900,306; and 5,080,650, to place tubes within the gastro-intestinal tract. These techniques typically involve a trans-oral approach of placing a gastro-intestinal tube in the patient's mouth and snaking it down the esophagus, into the stomach, and out the abdominal wall. Other techniques involve percutaneously inserting a tube into the stomach from outside of the abdominal wall by sliding the tube over a guidewire.

Practitioners have encountered numerous problems with the trans-oral techniques, which are complicated and cumbersome, often requiring more than one person to perform. Many of the problems are caused by dragging the gastro-intestinal tube through the anatomy. Problems such as patient discomfort, esophageal trauma, internal bleeding, and gastro-esophageal reflux condition, are caused or exacerbated by dragging of the gastro-intestinal tube through the esophagus. In addition, the risk of abdominal infection is increased due to the dragging of the gastro-intestinal tube through non-sterile areas such as the mouth and esophagus prior to placing the tube in the gastric and abdominal walls.

Practitioners have also experienced problems with techniques involving the percutaneous insertion of a tube. Some such problems are due to the fact that there is often no retention of the stomach wall's position with respect to axis of insertion. The stomach wall is often pushed distally during insertion, causing it to drift away from the abdominal wall. As the gastric wall drifts, the site chosen for tube placement within the gastric wall is lost. The lack of retention of the gastric wall makes dilation of the abdominal and gastric walls difficult, and allows for unintentional and undesirable pneumoperitoneum.

Other problems experienced with percutaneous insertion techniques are caused by the sequential insertion of dilation devices that is often involved. The abdominal wall, which is not particularly suited to sequential dilation, is often traumatized during the process. In addition, the sequential passage of devices prolongs the time needed to perform placement, and potentially leads to undesirable pneumoperitoneum.

Therefore, it is desirable to provide an improved apparatus and method for the placement of gastro-intestinal tubes, and more generally, the placement of any internal medical device.

SUMMARY OF THE INVENTION

In an embodiment, a medical device insertion apparatus includes an access tube defining a central lumen and a retention portion disposed at a distal end of the access tube. The retention portion is reconfigurable between a first configuration of reduced lateral extent and a second configuration of increased lateral extent. A trocar is moveably disposed within the central lumen of the access tube. The access tube is movably disposed within a central lumen of an overtube.

In an embodiment of a method of the present invention, the method includes the steps of inserting the trocar and access tube through a body wall of a patient, where the trocar is disposed within the access tube and where a retention portion disposed at a distal end of the access tube is configured in a first configuration of reduced lateral extent. The retention portion is then configured in a second configuration of increased lateral extent. The trocar is removed from the access tube. An overtube is inserted around the access tube and through the body wall, where the access tube is received within a central lumen of the overtube and where the retention portion is received through a slot defined by the overtube. The retention portion is returned to the first configuration of reduced lateral extent. The access tube is removed from the central lumen of the overtube and the medical device is inserted within the central lumen of the overtube and through the body wall. The overtube is then removed.

BRIEF DESCRIPTION OF THE DRAWINGS

The various features of the invention will best be appreciated by simultaneous reference to the description which follows and the accompanying drawings, in which.

DETAILED DESCRIPTION

Figure 1:
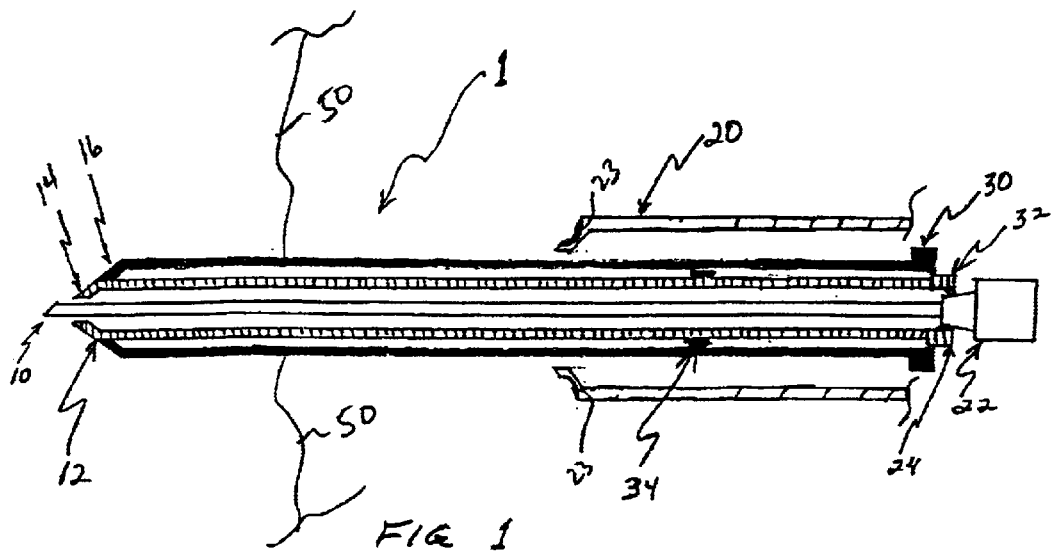
FIG. 1 is a side view, partially in section, of an embodiment of the medical device insertion apparatus of the present invention.

An embodiment of the medical device insertion apparatus 1 of the present invention, which in an exemplary embodiment will be described as a gastro-intestinal tube placement device, is shown in FIG. 1. The device includes a trocar 10, an access tube 12, and a dilating overtube 20. The placement device 1 is capable of engaging the patient's internal gastric wall during insertion, thereby preventing the gastric wall from drifting away from the patient's abdominal wall. The device 1 also allows a physician to place a gastro-intestinal tube percutaneously, without having to perform sequential dilation which can lead to many physiological maladies.

The trocar 10 and access tube 12 of the placement device 1 are formed such that they can be percutaneously inserted together as an assembly through the abdominal and gastric walls. The trocar 10 can be any of a variety of medical trocars having a distal end which is capable of penetrating the abdominal and gastric walls, e.g., a sharp distal end. During the insertion process, the distal end of the trocar 10 is used to initially penetrate the abdominal wall. The assembly of the trocar 10 and access tube 12 is then pushed distally until the assembly has sufficiently penetrated the gastric wall 50. Markings can be made on the outer surface of the access tube 12 to indicate the depth of insertion.

Figure 6:
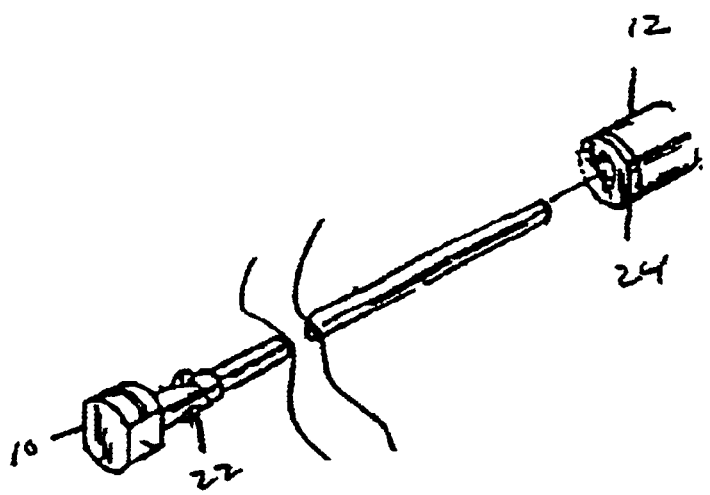
FIG. 6 is a perspective view of an embodiment of a locking mechanism of the trocar and access tube.

The trocar 10 and access tube 12 preferably have complementary mating parts 22, 24, respectively, of a locking mechanism, as can be seen at least in FIGS. 1 and 6, which prevents those components from moving with respect to each other during insertion. The locking mechanism is preferably a twisting hub assembly of the type shown in FIG. 6, but may be any mechanism for temporarily connecting the trocar 10 and access tube 12. Prior to insertion, the mating parts 22, 24 are engaged, thus locking the trocar 10 and access 12 tube together. Once the assembly is properly in-place within the gastric wall, the mating parts 22, 24 are disengaged, allowing removal of the trocar 10 from within the access tube 12.

The access tube 12 of the present invention is preferably formed of two concentric, slidable with respect to each other, malecot sheaths 14, 16, which are attached at their distal ends. Additionally, the access tube 12 has a retention portion 18 at its distal end, which is capable of being compressed or deactivated during insertion, and deployed or activated once the access tube 12 is properly placed within the gastric wall. The retention portion 18 can be made of wings such as those on a malecot-type catheter. In its deployed state, the retention portion 18 has a lateral extent which is greater than the diameter of the percutaneous penetration post-dilation. With this increased lateral extent, the practitioner performing the insertion process can pull the access tube 12 proximally, causing the retention portion 18 to engage the internal gastric wall, thereby preventing the gastric wall from drifting away from the abdominal wall.

Figure 2:
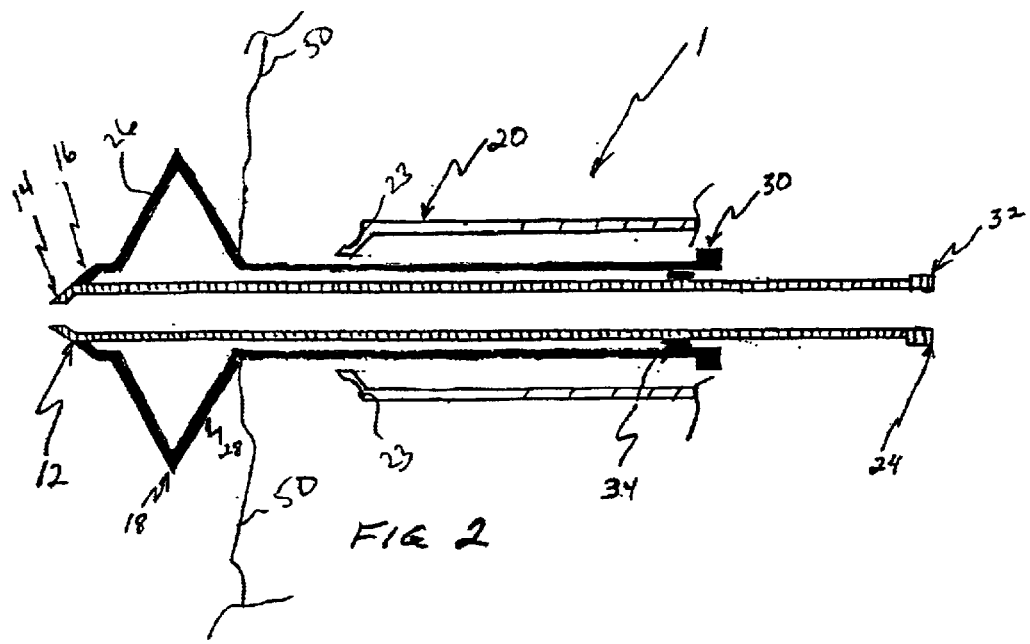
FIG. 2 is a side view, partially in section, of the embodiment of FIG. 1 with the retention portion in its deployed position.

In an embodiment, the distal retention portion 18 is deployed by unlocking mating sections 30 and 32 of outer malecot sheath 16 and inner malecot sheath 14, respectively, and then by moving the outer malecot sheath 16 distally with respect to the inner malecot sheath 14. The distal movement of the outer sheath 16 causes the distal portion of the access tube 12 to form lateral wings 26, 28, which are similar to those of other malecot sheaths. FIG. 2 illustrates the retention portion 18 of the access tube 12 in its deployed, or activated, state. Although there can be any number of wings, such as two wings 26 and 28, the deployed retention portion 18 preferably has a malecot-type shape. The lateral extent of the deployed retention portion 18 is sufficient to provide retention of the gastric wall during insertion of the dilating overtube 20.

As mentioned above, the inner sheath 14 and outer sheath 16 preferably have mating parts 32, 30, respectively, of a locking mechanism which allow the sheaths to be attached to each other and thereby avoid relative movement with respect to each other during initial insertion. This locking mechanism can also be a twisting hub assembly, similar in structure to mating parts 22, 24 of the locking mechanism illustrated in FIG. 6.

Whereas an embodiment of the present invention includes mating sections 30 and 32, it is not required that these mating sections be utilized in the present invention.

After initial insertion is complete and the trocar/access tube assembly is properly in place within the gastric cavity, as discussed above, the locking mechanism formed by mating parts 30 and 32 is disengaged, such as by untwisting the twisting hub assembly if a twisting hub assembly is utilized for the locking mechanism or by pushing the outer sheath 16 distally with respect to inner sheath 14 and uncoupling a tapered, frictional engagement form-fitted structure that comprises mating parts 30 and 32. The outer sheath 16 is pushed distally to bring the additional mating locking part 34 of inner sheath 14 into contact with the mating part 30 of the outer sheath 16. By engaging mating parts 30 and 34, the sheaths 14 and 16 are locked in position with the distal retention portion 18 deployed.

Again, any number of various configurations for mating parts, and thus for locking hubs, can be utilized in the present invention. For example, a slide lock similar to the type used on various handles for temporary locking of two pieces together relative to each other can be utilized in the present invention. Additionally, locking hubs such as those tightened on the outside diameter of various catheters can be used.

Figure 3:
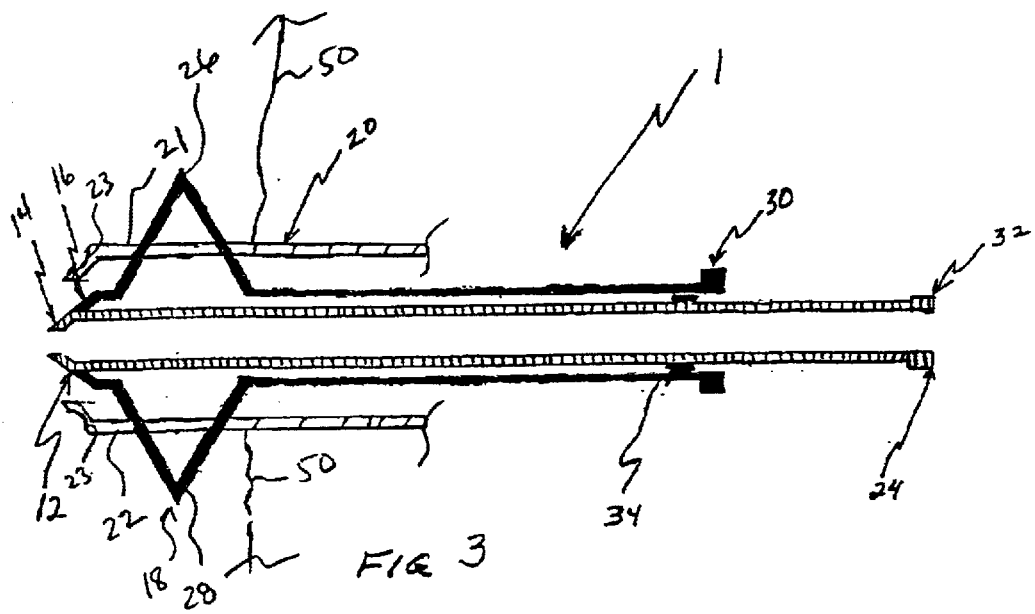
FIG. 3 is a side view, partially in section, of the embodiment of FIG. 1 with the overtube disposed around the access tube with the retention portion in its deployed position.

The dilating overtube 20 is a tubular structure with a central lumen capable of passing over the access tube 12, with or without the trocar 10 within the access tube 12. As can be seen in FIG. 3, during the overtube insertion process, the overtube 20 is advanced distally over the access tube 12 until it is properly placed within the gastric wall. Preferably, the overtube 20 has slots 21, 22 at its distal end which are capable of receiving within them the deployed wings 26, 28, respectively, of the distal retention portion 18 when the overtube 20 is distally advanced over the access tube 12.

The distal end of the overtube 20 is tapered to facilitate advancement of the overtube 20 through the patient's anatomy. The overtube 20 may also have a small circumferential groove 23 at its distal end which could be grasped by an endoscopic snare. In order to facilitate distal advancement of the overtube 20 during its insertion, an endoscope having a snare can be placed within the gastric cavity. The practitioner performing the insertion process can then pull the snare, causing the overtube 20 to advance distally into the gastric cavity.

Figure 4:
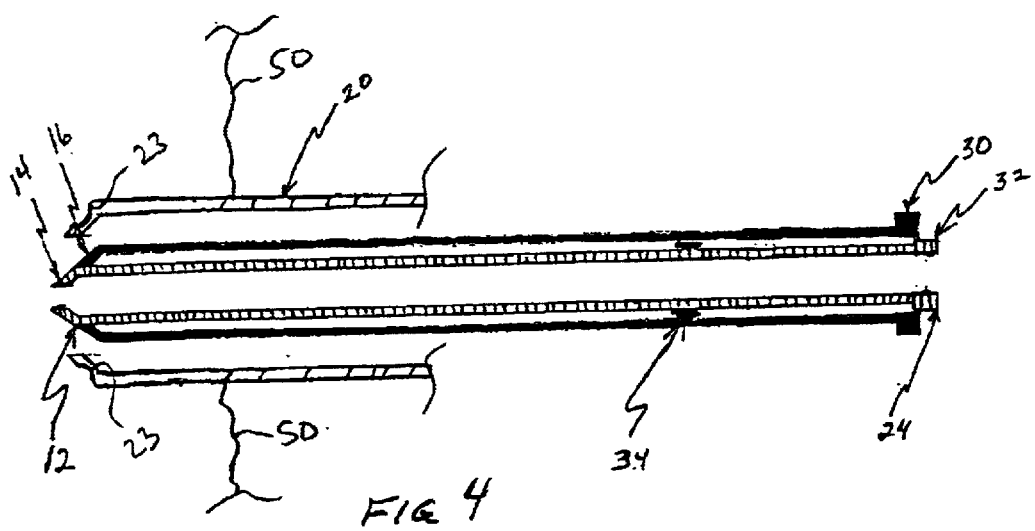
FIG. 4 is a side view, partially in section, of the embodiment of FIG. 1 with the overtube disposed around the access tube with the retention portion in its deactivated position.
Figure 5:
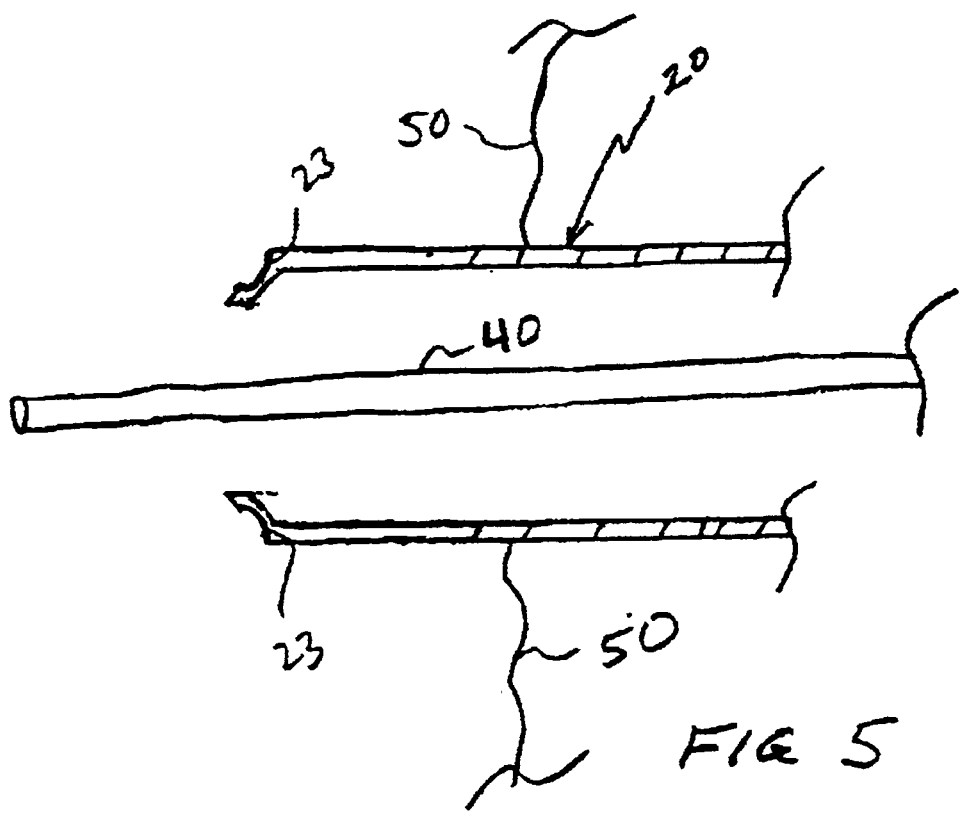
FIG. 5 is a side view, partially in section, of the embodiment of FIG. 1 with the access tube removed from the overtube and with a gastro-intestinal tube inserted through the overtube.

Once the overtube 20 is properly placed, the retention portion 18 of the access tube 12 is compressed, or deactivated, by unlocking mating parts 30 and 34 and moving outer sheath 16 proximally with respect to inner sheath 14, as can be seen in FIG. 4. Deactivation of retention portion 18 allows removal of the access tube 12 from within the penetration. With the distal portion of the overtube 20 in place within the gastric cavity, as can be seen in FIG. 5, a gastro-intestinal tube 40 can be inserted into the gastric cavity by first placing the gastro-intestinal tube 40 within the central lumen at the proximal end of the overtube 20 and then pushing the gastro-intestinal tube 40 distally until it exits the distal end of the overtube 20.

The distal dilating tip of the overtube could be comprised such that it could expand if a device having a larger diameter than that of the distal dilating tip were required to be inserted through it. This expansion could be achieved by comprising the dilating tip of a semi-flexible material, providing longitudinal slits in the dilating tip, by utilizing a combination of the these two techniques, or through other known methodologies.

After the distal end of the gastro-intestinal tube has exited the distal end of the overtube 20, the overtube would be removed by sliding the overtube proximally in relation to the gastro-intestinal tube. The gastro-intestinal tube remains in position in the gastric cavity due to any number of known retention mechanisms. The gastro-intestinal tube is then left in place, percutaneously inserted into the gastric cavity.

Figure 7:
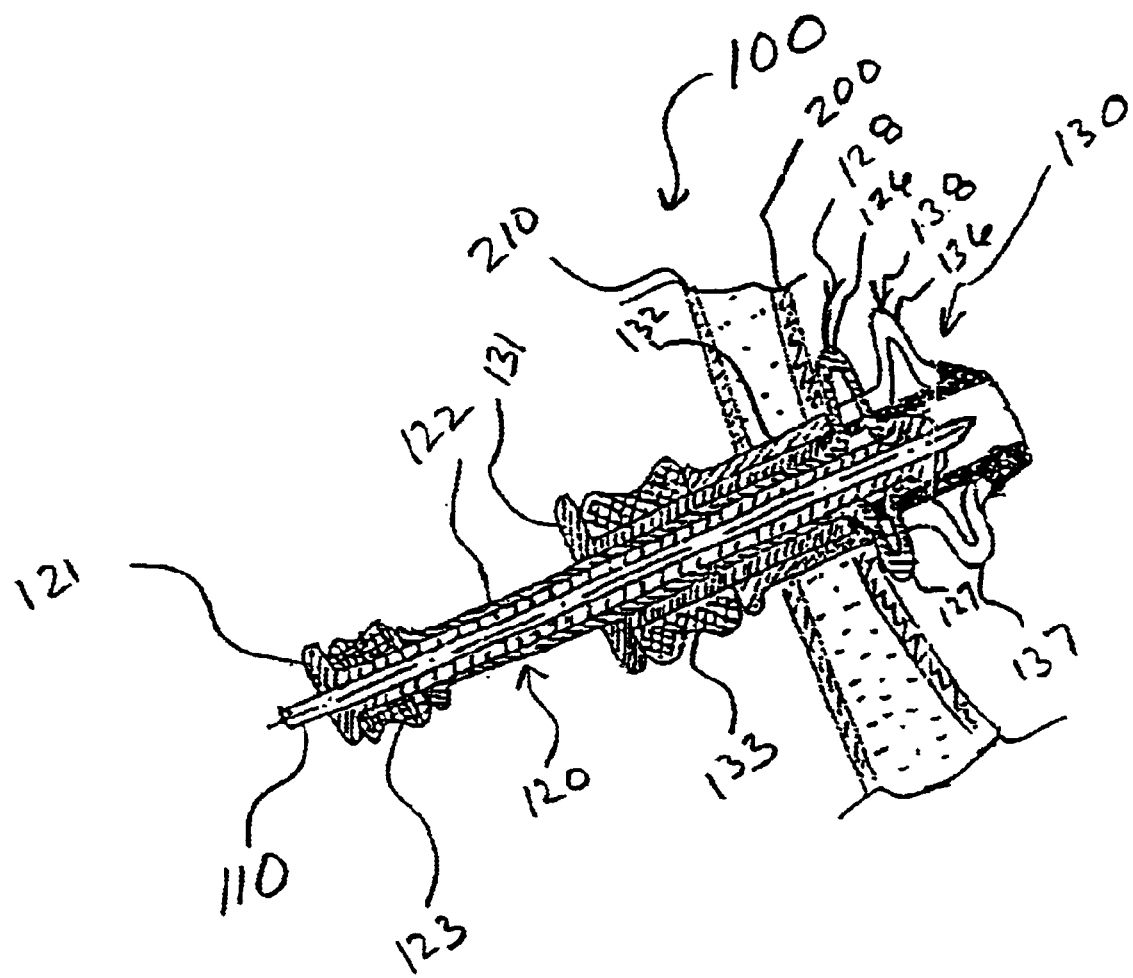
FIG. 7 is a side view, partially in section, of an alternative embodiment of the medical device insertion apparatus of the present invention.

FIG. 7 illustrates an alternative embodiment of a medical device insertion apparatus 100 of the present invention. In the embodiment of FIG. 7, the dilating overtube 130 also includes a retention portion 138. Retention portion 138 is included in addition to retention portion 128 of access tube 120. Retention portion 138 provides an additional mechanism for anchoring the overtube 130 within the gastric cavity and maintaining the relative positioning of the gastric wall 200 with respect to the abdominal wall 210 during removal of the access tube and/or passage of a gastro-intestinal tube through the lumen of the overtube.

As can be seen in FIG. 7, retention portion 138 may consist of laterally extending wings 136, 137 of malecot-type, which may be similar to wings 26, 28 of the previous embodiment. Additionally, retention portion 128 of access tube 120 may also consist of laterally extending wings 126, 127 of malecot-type, which also may be similar to wings 26, 28. Both retention portion 128 and retention portion 138 are moveable between a first configuration of reduced lateral extent and a second configuration of increased lateral extent. Retention portions 128 and 138 are moved between their first and second configurations in the same manner as was described for retention portion 18. Similar to the previously described embodiment, overtube 130 includes slots in its distal end to provide for receiving the deployed wings of retention portion 128 within them.

In the embodiment of FIG. 7, as in the previous embodiment, trocar 110 is movably disposed within access tube 120. Access tube 120 includes an inner sheath 121 and an outer sheath 122. Retention portion 128 is disposed at a distal end of outer sheath 122. Retention portion 128, in its second configuration, as described above, extends through an aperture, or slots, included in the distal end of overtube 130.

Overtube 130 also includes an inner sheath 131 and an outer sheath 132. Retention portion 138 is disposed at the distal end of outer sheath 132. Retention portion 138, in its second configuration, is disposed distally of retention portion 128.

Finger grips 123 and 133 are provided on access tube 120 and overtube 130, respectively, to aid in medical device insertion apparatus 100.

As described above, in practicing a method in accordance with the principles of the present invention, the method includes the steps of inserting the trocar and access tube through a body wall of a patient, where the trocar is disposed within the access tube and where a retention portion disposed at a distal end of the access tube is configured in a first configuration of reduced lateral extent. The retention portion is then configured in a second configuration of increased lateral extent and pulled outward to compress, in an embodiment, the gastric, or stomach, wall against other body tissues, e.g., the abdominal wall. The trocar is removed from the access tube. An overtube is inserted around the access tube and through the body wall, where the access tube is received within a central lumen of the overtube and where the retention portion is received through a slot defined by the overtube. The retention portion is returned to the first configuration of reduced lateral extent. The access tube is removed from the central lumen of the overtube, the overtube is pushed inward, in an embodiment, to maintain access as the stomach assumes a normal position in the body in the absence of being retained by the retention portion of the access tube, and a medical device is inserted within the central lumen of the overtube and through the body wall. The overtube is then removed.

The disclosed embodiments are illustrative of the various ways in which the present invention may be practiced. Other embodiments can be implemented by those skilled in the art without departing from the spirit and scope of the present invention. For example, whereas an apparatus and method of the present invention has been described for use in the percutaneous placement of a gastro-intestinal device, e.g., a gastro-intestinal tube through the gastric wall, the principles of the present invention can be utilized for placement of any type of device into any hollow internal organ. Examples of other hollow internal organs into which devices can be inserted with the present invention include the liver, kidney, small or large intestine, bladder, etc.

What is claimed is:

1. A medical device insertion apparatus, comprising:
an access tube defining a central lumen and a retention portion disposed at a distal end of the access tube, the retention portion reconfigurable between a first configuration of reduced lateral extent and a second configuration of increased lateral extent;
a trocar movably disposed within the central lumen of the access tube; and
an overtube defining a central lumen, the access tube movably disposed within the central lumen of the overtube, the overtube having at least one side opening adapted to permit the retention portion to project therethrough,
wherein the trocar includes a connector portion at a proximal end thereof and wherein the access tube includes a mating connector portion at a proximal end thereof, the connector portion couplable with the mating connector portion such that when coupled the trocar is rigidly joined to the access tube.

2. The medical device insertion apparatus of claim 1 wherein the access tube includes a first sheath and a second sheath, the first sheath movably disposed within the second sheath.

3. The medical device insertion apparatus of claim 1 wherein the retention portion includes a first wing and a second wing.

4. The medical device insertion apparatus of claim 3 wherein the at least one side opening of the overtube includes a first slot and a second slot and wherein, when the retention portion is in its second configuration of increased lateral extent, the first wing is receivable within the first slot and the second wing is receivable within the second slot.

5. The medical device insertion apparatus of claim 1 wherein the overtube includes a retention portion disposed at a distal end of the overtube and wherein the retention portion of the overtube is reconfigurable between a first configuration of reduced lateral extent and a second configuration of increased lateral extent.

6. The medical device insertion apparatus of claim 2 wherein the first sheath includes a connector and wherein the second sheath includes a connector, the connector of the first sheath couplable with the connector of the second sheath.

7. The medical device insertion apparatus of claim 2 wherein the retention portion is configured in the second configuration of increased lateral extent by moving the second sheath distally with respect to the first sheath.

8. The medical device insertion apparatus of claim 6 wherein the first sheath includes a second connector, the second connector of the first sheath disposed distally of the first connector of the first sheath, and wherein the second connector of the first sheath is couplable with the connector of the second sheath.

9. The medical device insertion apparatus of claim 2 wherein the retention portion is formed on the second sheath of the access tube.

10. A method of inserting a medical device into a patient comprising the steps of:

inserting a trocar and access tube through a body wall of the patient, wherein the trocar is disposed within the access tube and wherein a retention portion disposed at a distal end of the access tube is configured in a first configuration of reduced lateral extent;

configuring the retention portion in a second configuration of increased lateral extent;

removing the trocar from the access tube;

inserting an overtube around the access tube and through the body wall, wherein the access tube is received within a central lumen of the overtube and wherein the retention portion is received through a slot defined by the overtube;

configuring the retention portion in the first configuration of reduced lateral extent;

removing the access tube from the central lumen of the overtube; and inserting the medical device within the central lumen of the overtube and through the body wall.

11. The method of claim 10 further comprising the step of coupling the trocar to the access tube.

12. The method of claim 10 wherein the access tube includes a first sheath and a second sheath and wherein the step of inserting the trocar and access tube through the body wall of the patient includes the steps of rigidly coupling the first sheath to the second sheath and rigidly coupling the trocar to the access tube.

13. The method of claim 10 wherein the access tube includes a first sheath and a second sheath and wherein the step of configuring the retention portion in a second configuration of increased lateral extent includes the step of moving the second sheath distally with respect to the first sheath.

14. The method of claim 10 wherein a retention portion is disposed at a distal end of the overtube and further comprising the step of configuring the retention portion of the overtube in a configuration of increased lateral extent after the step of inserting the overtube around the access tube and through the body wall.

15. The method of claim 10 wherein the medical device is a gastro-intestinal tube.

16. The method of claim 15 wherein the body wall includes an abdominal wall and a gastric wall.

* * * * *